United States Patent [19]
Bushnell et al.

[11] Patent Number: 5,888,835
[45] Date of Patent: Mar. 30, 1999

[54] METHOD AND APPARATUS FOR WASH, RESUSPENSION, RECOLLECTION AND LOCALIZATION OF MAGNETIZABLE PARTICLES IN ASSAYS USING MAGNETIC SEPARATION TECHNOLOGY

[75] Inventors: Steven E. Bushnell, Medfield, Mass.; Tina K. Garyantes, Warren, N.J.; Michael L. Malek, North Olmsted, Ohio; Howard J. Kirchick, San Diego, Calif.

[73] Assignee: Chiron Diagnostics Corporation, East Walpole, Mass.

[21] Appl. No.: 644,909

[22] Filed: May 10, 1996

[51] Int. Cl.⁶ .................................................. G01N 33/553
[52] U.S. Cl. .......................... 436/526; 209/214; 210/695; 210/222; 422/65; 435/287.1; 435/287.2; 435/287.3; 436/47; 436/807; 436/809
[58] Field of Search ............................ 209/214; 210/695, 210/222; 422/65; 435/287.1, 287.2, 287.3; 436/526, 47, 807, 809

[56] References Cited

U.S. PATENT DOCUMENTS

| | | | |
|---|---|---|---|
| 4,265,855 | 5/1981 | Mandle et al. | 422/65 |
| 4,628,037 | 12/1986 | Chagnon et al. | 436/526 |
| 4,661,408 | 4/1987 | Lau et al. | 428/405 |
| 4,698,302 | 10/1987 | Whitehead et al. | 435/94 |
| 4,745,077 | 5/1988 | Holian et al. | 436/526 |
| 4,785,407 | 11/1988 | Sakagami | 364/497 |
| 5,104,808 | 4/1992 | Laska et al. | 436/48 |
| 5,108,933 | 4/1992 | Liberti et al. | 436/501 |
| 5,128,103 | 7/1992 | Wang et al. | 422/64 |
| 5,147,529 | 9/1992 | Lee et al. | 210/695 |
| 5,183,638 | 2/1993 | Wakatake | 422/64 |
| 5,186,827 | 2/1993 | Liberti et al. | 210/222 |
| 5,200,084 | 4/1993 | Liberti et al. | 210/695 |
| 5,232,665 | 8/1993 | Burkovich et al. | 422/65 |
| 5,256,532 | 10/1993 | Melnicoff et al. | 435/5 |
| 5,278,080 | 1/1994 | Midgley et al. | 436/500 |
| 5,283,079 | 2/1994 | Wang et al. | 427/2 |
| 5,374,531 | 12/1994 | Jensen | 435/7.24 |
| 5,395,688 | 3/1995 | Wang et al. | 428/327 |
| 5,466,574 | 11/1995 | Liberti et al. | 435/5 |
| 5,491,068 | 2/1996 | Benjamin et al. | 435/7.32 |

FOREIGN PATENT DOCUMENTS

| | | |
|---|---|---|
| 0358948 | 3/1990 | European Pat. Off. . |
| 0371265 | 6/1990 | European Pat. Off. . |
| 0410645 | 1/1991 | European Pat. Off. . |
| 0589636 | 3/1994 | European Pat. Off. . |

OTHER PUBLICATIONS

Advanced Magnetics Inc. (Jul. 1984) "Instructions and Precautions for Handling Biomag".

*Primary Examiner*—Susan Wolski
*Attorney, Agent, or Firm*—Arthur S. Morgenstern; Charles L. Gagnebin, III; Robert P. Blackburn

[57] ABSTRACT

Method and apparatus for enabling resuspension wash and magnetic localization of sample components bound to particles with magnetic properties in reaction vessels during separation and wash for enhanced chemiluminescent signal generation in biomedical assays. The assays involve moving reaction vessels past magnetic arrays that partially localized the particles prior to passing a gap where washing occurs, with or without resuspension, after separating out the unbound components and liquid. The band of particles is further localized by a focusing magnet at the end of the array prior to dosing the vessel with acid for chemiluminescent purposes. A block of soft magnetic material is employed in place of a magnet in the gap to minimize magnetic strength at the gap. Trimmed magnets adjacent the gap cause left, then right, particle shifting that localizes the magnetizable particles. The gap enables improved resuspension by wash, whereas the localized particles enable more efficient resuspension by reagent.

23 Claims, 3 Drawing Sheets

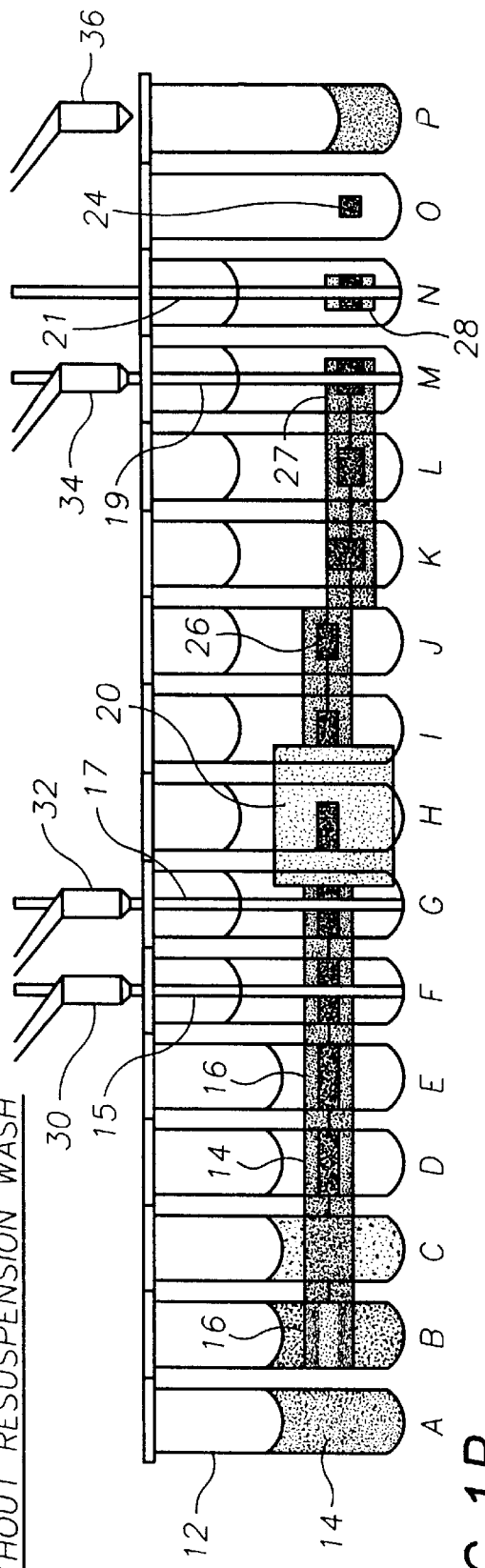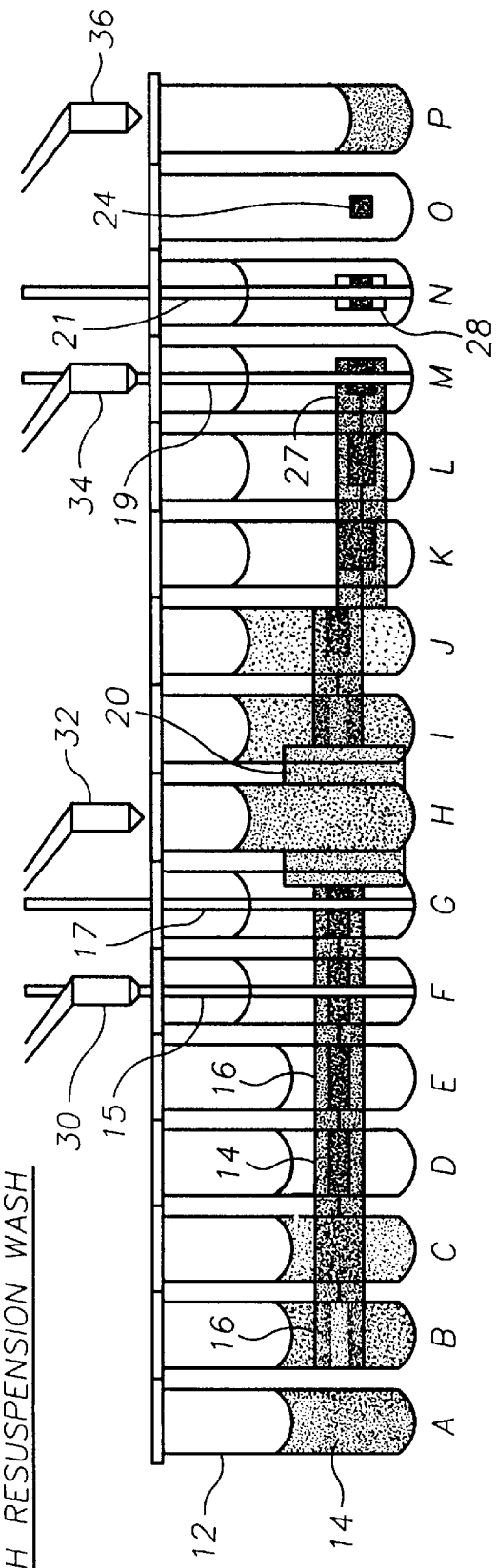

METHOD AND APPARATUS FOR WASH, RESUSPENSION, RECOLLECTION AND LOCALIZATION OF MAGNETIZABLE PARTICLES IN ASSAYS USING MAGNETIC SEPARATION TECHNOLOGY

FIELD OF THE INVENTION

The invention generally relates to the field of biomedical assays employing magnetic separation techniques, and specifically to a method and apparatus for focusing or localizing magnetizable particles during separation and wash in such assays.

BACKGROUND OF THE INVENTION

Heterogeneous immunoassays typically require the separation of sought-for components bound to component-selective particles from unbound or free components of the assay. To increase the efficiency of this separation, many assays wash the solid phase (the bound component) of the assay after the initial separation (the removal or aspiration of the liquid phase). Some chemiluminescent immunoassays use magnetic separation to remove the unbound assay components from the reaction vessel prior to addition of a reagent used in producing chemiluminescence or the detectable signal indicative of the amount of bound component present. This is accomplished by using magnetizable particles including, but not restricted to, paramagnetic particles, superparamagnetic particles, ferromagnetic particles and ferrimagnetic particles. Tested-for assay components are bound to component-specific sites on magnetizable particles during the course of the assay. The associated magnetizable particles are attracted to magnets for retention in the reaction vessel while the liquid phase, containing unbound components, is aspirated from the reaction vessel.

Washing of the solid phase after the initial separation is accomplished by dispensing and then aspirating a wash buffer while the magnetizable particles are attracted to the magnet.

Greater efficiency in washing is accomplished by moving the reaction vessels along a magnet array having a gap in the array structure proximate a wash position, allowing the magnetizable particles to resuspend during the dispense of the wash buffer. This is known as resuspension wash. Subsequent positions in the array include magnets, allowing the magnetizable particles to recollect prior to aspiration of the wash buffer and introduction of reagent beyond the end of the magnet array.

One prior art wash block configuration provides an aluminum insert in the gap of the magnet array at the wash position. Rather than simply removing a magnet from the resuspension position, the insert prevents a reaction vessel from becoming misaligned and jammed in the magnet array. While functioning adequately for assays which employ resuspension wash, it is evident that the provision of an aluminum insert in place of a magnet at the wash position adversely effects assays which do not use the resuspension in washing but which proceed through the wash position without resuspension. A single band of magnetizable particles which is normally formed along the interior of the reaction vessel as it passes the magnet array, during the initial separation, is split into two smaller bands on either side of the reaction vessel due to attraction by the magnets on either side of the insert at the resuspension and wash position. Since the reagent is introduced into the reaction vessel in a stream directed toward where the magnetizable particles collected before splitting, the split in the banding of the magnetizable particles results in the stream missing the main concentration of magnetizable particles. Poor resuspension of the magnetizable particles during resuspension wash and upon addition of an acid reagent used to condition the bound component reagent in the generation of a chemiluminescent signal results.

Therefore, the prior art fails to provide a wash region which enables the efficient washing of magnetizable particles during the wash phase of a magnetic separation assay without adversely effecting assays not employing resuspension wash.

SUMMARY OF THE INVENTION

It is an object of the present invention to provide methods and apparatus for focusing or localizing magnetizable particles during separation and wash for enhanced signal generation in assays which use magnetic separation technology. It is a further object of the present invention to provide a wash region enabling enhanced suspension of solid phase components for a sample, regardless of whether it undergoes resuspension wash.

These objects are achieved by employing an insert of soft magnetic material in place of separation magnets at a wash position in the array, wherein the insert has a width greater than the width of a reaction vessel passing thereby. Further, the magnets of the array both up and downstream of the wash position terminate at locations intermediate the reaction vessel for enhanced focusing of magnetizable particles in the path of a reagent stream, resulting in improved resuspension of the magnetizable particles by the reagent. Therefore, resuspension wash efficiency is enhanced, and magnetizable particle focusing is increased, leading to a more efficient magnetizable particle resuspension for the signal generation portion of the assay.

At the end of the magnet array, a focusing magnet having a face dimension less than a vessel width is employed in the array to more completely localize the magnetizable particles prior to being in the path of an injected acid stream employed to initiate the reaction leading to chemiluminescence.

For assays not employing resuspension wash, the provision of the soft magnetic insert results in avoidance of split banding of the magnetizable particles, while magnetizable particle focusing results in improved chemiluminescent reaction.

For assays employing resuspension wash, the soft magnetic insert enables resuspension wash while avoiding premature collection and splitting of magnetizable particles due to the influence of magnets adjacent to the wash position. As with assays not employing resuspension wash, magnetizable particle focusing results in improved chemiluminescent reaction.

BRIEF DESCRIPTION OF THE DRAWINGS

This invention is pointed out with particularity in the appended claims. The above and further advantages may be more fully understood by referring to the following description and accompanying drawings of which:

FIG. 1A is an elevation view of a magnet array and a sequence of reaction vessels passing therethrough according to the present invention;

FIG. 1B is an elevation view of the magnet array of FIG. 1A in which resuspension wash is performed;

DETAILED DESCRIPTION

Figure 2:
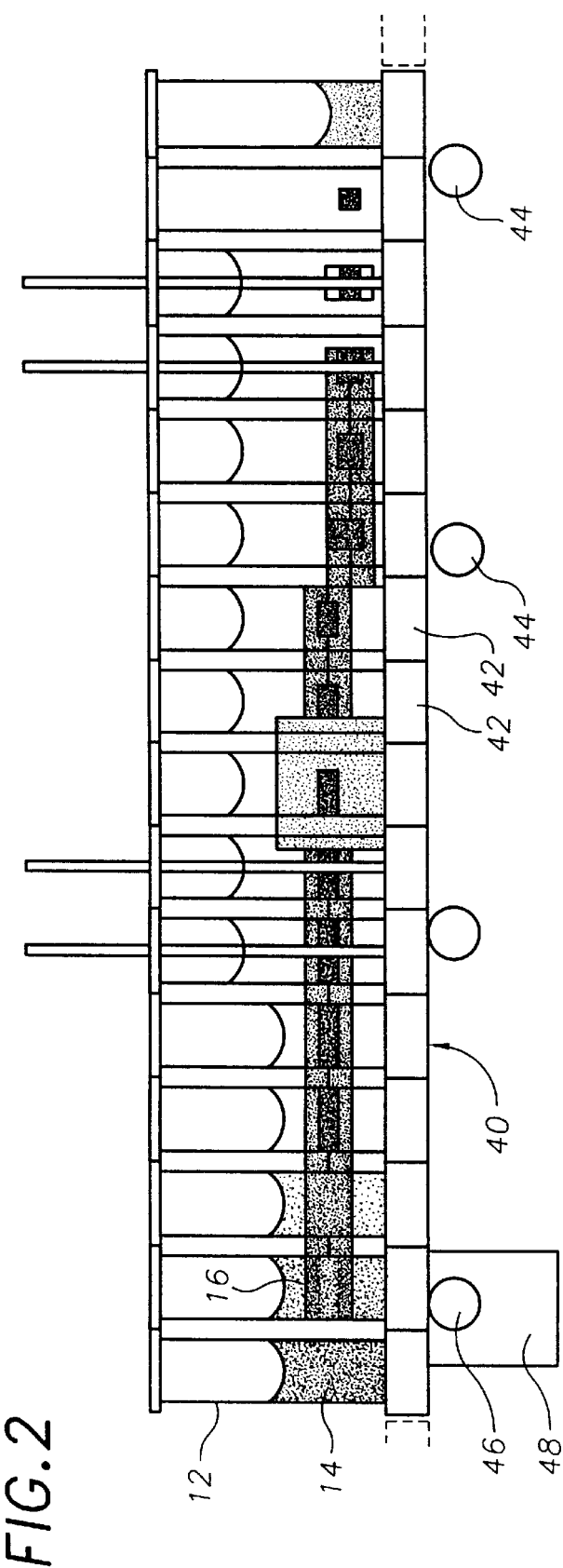
FIG. 2 is an elevation view of the magnet array of FIG. 1A illustrating a reaction vessel transport mechanism.

To increase the efficiency of the separation of bound components from free components in immunoassays, many assays wash the solid phase (bound component) of the assay after the initial separation (removal of the liquid phase and unbound component). The present invention operates in the context of a chemiluminescent immunoassay of known type which uses magnetic separation to remove unbound assay components from a reaction vessel such as a cuvette.

The presently disclosed method and apparatus enables a resuspension wash of magnetizable particles with improved wash efficiency and focuses magnetizable particles from a band to a small region or dot, enabling a more efficient resuspension of magnetizable particles for a signal generation portion of the assay.

In all of the following discussions, it is assumed that the reaction vessels progress from the left-hand side of the illustrations to the right-hand side past a fixed magnet array at regularly timed intervals, although continuous motion is not excluded. Means for imparting lateral translation of the reaction vessels is described subsequently with regard to FIG. 2. In an exemplary embodiment, such interval is approximately 15 seconds. Additionally, throughout this description, aspiration and dispense functions are executed via means known in the art without full details being shown.

The magnet array of FIGS. 1A and 1B includes a succession of reaction vessels such as cuvettes 12, each containing assay components and magnetizable particles 14 which are initially in a freely distributed state within the respective cuvette 12. The concentration of solid phase (bound component) of the assay remaining in free suspension in the cuvette at position B is less than that of the first cuvette 12 in position A due to the initial collection of solid phase proximate magnets of the array 16 at position B. In the cuvette 12 of position C, this effect is more evident. By the time a cuvette has progressed to position D, the majority of the solid phase 14 has collected proximate respective magnets of the array 16.

References to "magnets" adjacent a respective position are understood to refer to a pair of adjacent magnets of oppositely oriented polarity, one above the other, proximate the respective cuvette position. A band of magnetizable particles 14 forms along the junction of these two magnets, where the magnetic gradient is at a maximum.

Non-resuspension washes are provided at positions F, G, and M in the illustrative embodiment of FIG. 1A, and at positions F and M in the embodiment of FIG. 1B. At these positions, liquid phase is aspirated from the cuvette 12 via tubes (15, 17, 19 in FIG. 1A and 15, 19 in FIG. 1B) and wash buffer is reintroduced via nozzles (30, 32, 34 in FIG. 1A and 30, 34 in FIG. 1B). The nozzles are positioned in front of respective tubes in the view of FIGS. 1A and 1B. In particular, the nozzles are angled toward the front of the respective cuvette 12 (out of the page in FIGS. 1A and 1B-See FIG. 4B) to avoid disturbing the pellet of solid phase 14 collected at the respective magnets of the array 16.

The tube 21 at position N of FIGS. 1A and 1B is employed to aspirate liquid phase from the respective cuvette 12 prior to the introduction, at position P, of reagent via nozzle 36, the reagent facilitating a subsequent chemiluminescent reaction within a luminometer. In contrast to the non-resuspension wash nozzles (30, 32, 34 in FIG. 1A and 30, 34 in FIG. 1B), the reagent dispensing nozzles 36 are angled toward the pellet of solid phase 14 in order to thoroughly disperse it, as shown in FIG. 4B.

In prior art magnet arrays, a portion of the liquid phase may remain trapped within the solid phase 14 prior to introduction of the reagent at position P, even after repeated non-resuspension washes, such as at positions F, G, and M in FIG. 1A and positions F and M in FIG. 1B. This trapped liquid phase limits the accuracy of the assay.

At position K of FIG. 1A, the magnets of the array 16 proximate the cuvettes 12 are disposed at a lower position. This provides the solid phase pellet 14 with time to recollect at the lower position prior to the introduction of assay reagent at position P. Thus, when reagent is directed at the pellet 14 in position P by the nozzle 36, the solid phase 14 will be centrally located in the reaction vessel 12 when the acid is applied at position P. However, such repositioning of the pellet does not necessarily enhance the ability of the non-resuspension washes to rid the solid phase 14 of trapped liquid phase.

In FIG. 1A, a resuspension wash is not employed, and as such the focused, or localized, solid phase remains proximate respective magnets 16 as the cuvette 12 progresses through the wash block.

In contrast, the magnet array of FIG. 1B does employ a resuspension wash. Resuspension washing of the solid phase involves the aspiration of the liquid phase containing the unbound components of the assay from the cuvette 12 at position G via the tube 17 while the bound components are held in place by respective magnets in the array 16. This is followed by re-introduction of wash buffer into the cuvette 12 at position H by a dispense nozzle 32 angled at the solid phase pellet 14 collected at the back of the cuvette 12 proximate the magnets 16.

At position H, magnets of the array 16 have been replaced by a soft magnetic insert 20. By dispensing wash buffer onto the magnetizable particles via the nozzle 32 in the absence of magnets in the array 16, the magnetizable particles are resuspended, exposing more surface area, and freeing liquid phase trapped during initial magnetizable particle collection. After the solid phase has been resuspended, it is recollected by a subsequent series of magnets in the array 16 at positions I et seq. prior to aspiration of the wash buffer and introduction of the acid reagent at position P. Other wash stages, in addition to those illustrated, are possible.

The wash block of FIGS. 1A and 1B is provided with a large gap in the magnet array at position H, thus enhancing resuspension wash. Prior art magnet arrays employed narrower gaps, resulting in split bands of magnetizable particles due to the attractive forces of array magnets on either side of the narrow gap.

The present invention avoids the splitting of the solid phase material into bands at opposite sides of the cuvette 12, in part, by providing a focusing of the solid phase 14 into a smaller band or dot 24. The gap at the resuspension wash position is filled with an insert 20 made of a soft magnetic material such as low carbon steel. "Soft magnetic material" is a term known in the art to mean materials which are relatively easily magnetized or demagnetized, and which have low hysteresis loss, high permeability, and low coercive force. Further, the magnets of the array 16 at positions G and I on either side of the resuspension wash position, position H, are trimmed such that the gap in the array of magnets 16 and the insert 20 extend proximate a region of the reaction vessels 12 previously occupied by the solid phase band 14 adjacent to the resuspension wash position.

As a result, magnetizable particles linearly banded by the magnets in the previous positions, but which are no longer directly aligned with magnets of the array 16, migrate along the reaction vessel 12 walls towards portions of the reaction vessel interior proximate the trimmed magnets 16. For instance, in position G, the magnets 16 are trimmed on the right-hand side. Magnetizable particles formerly aligned in the trimmed region now migrate to the center of the vessel 12, over the trimmed magnets 16.

The magnetizable particle banding pattern in the reaction vessel at the resuspension wash position, position H, remains unchanged in the absence of resuspension wash (FIG. 1A). With resuspension wash (FIG. 1B), the large soft magnetic insert 20 enables the complete resuspension of the solid phase 14 free of influence of magnets at positions G and I. Also, the provision of magnets trimmed on a left-hand side at position I downstream of the resuspension wash position, position H, further serves to avoid influencing the magnetizable particles during the resuspension wash in FIG. 1B.

The array 16 magnets at position I, downstream of the resuspension wash position, position H, and the soft magnetic insert 20, is also trimmed on its left-hand side in FIG. 1A. This serves to focus the solid phase 14 downstream of the resuspension wash position, position H. The magnetizable particles on the left side of the reaction vessel 12 are no longer directly aligned with magnets 16 at position I. Rather, they migrate toward the right, into the center of the vessel 12. The net effect is a conversion of the magnetizable particles from a wide band 14 to a more compact, centrally located band 26.

For the embodiment of FIG. 1A, the single magnetizable particle band at position H does not split into two bands as in the prior art because the soft magnetic insert 20 acts to short out, or minimize, the magnitude of the field gradient in the resuspension wash position, position H, and because trimming the magnets of the array 16 at positions G and I reduces the reach of the fields, from the same, into the resuspension position H.

At position M, trimmed magnets 27 are provided to further narrow the band of collected magnetizable particles. In a further embodiment, even smaller magnets 28, focusing magnets, are employed at position N to focus the magnetizable particles into yet a smaller area, thus providing a smaller target of solid phase 24 at position P for more efficient resuspension upon dispense of reagent. Smaller, focusing magnets 28 are not used in a preferred embodiment for the initial collection of the solid phase because, amongst other things, the larger the magnet surface area, the faster the collection of the magnetizable particles.

In an alternative embodiment, all of the magnets in the array 16 along the length of the wash block are provided as focusing magnets 28, though the resuspension wash position, position H, would continue to be provided with a gap such as that provided by the soft magnetic block 20 of FIGS. 1A and 1B. However, such an embodiment would require more time for each reaction vessel 12 to be proximate the magnets 28 in the array to provide an equivalent degree of capture capability due to the smaller size of the magnets in such an embodiment.

In yet another embodiment of the present invention, it is possible to enable further focusing of the magnetizable particles by employing another gap in the magnet array 16 prior to the focusing magnets 28 at position N. For instance, such a gap could be employed at position L. Here, the magnetizable particles 14 have already been gathered at an interior wall of the reaction vessel 12. A gap at position L would allow the magnetizable particles to become released from the interior wall, though they would generally remain localized. Thus, re-attraction by subsequent focusing magnets 38 would not take an excessive amount of time.

Illustratively, in a first embodiment illustrated in FIG. 2, the reaction vessels 12 containing the suspended solid phase 14 are laterally translated along the magnet array 16 by a linked conveyor belt 40 comprised of a sequence of reaction vessel receptacles 42. A sequence of freely rotatable rollers 44 are employed to provide support for the conveyor belt 40. At least one such roller 46 is mechanically connected to a motor 48, wherein the motor 48 rotates this roller 46, which in turn causes the conveyor belt 40 and the reaction vessels 12 disposed therein to translate relative to the magnet array 16.

Figure 3:
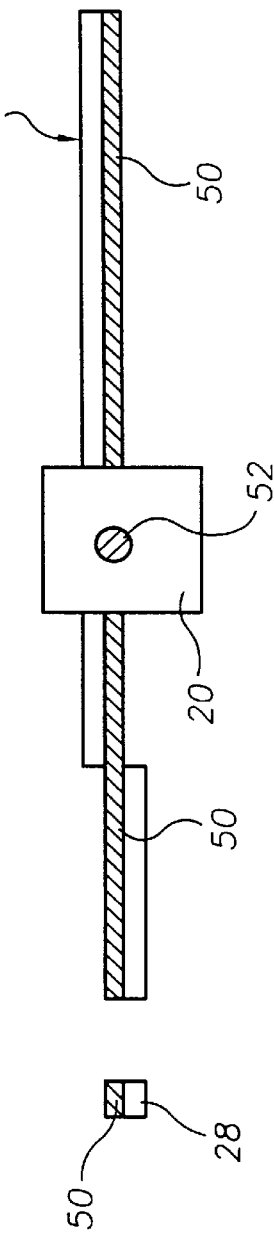
FIG. 3 is a rear elevation view of the magnet array of FIG. 1A illustrating a magnet array support structure.

The rear view of the magnet array in FIG. 3 illustrates a first embodiment of a magnet array 16 support structure 50. The magnet array 16 of FIG. 3 is a reverse view of the magnet array 16 of FIGS. 1A and 1B. The magnets of the array are backed by a conductive material such as high-iron, low-carbon steel to focus the magnetic field toward the reaction vessels 12. The support structure 50, which attaches to the magnet backing material, is preferably provided from a magnetically non-reactive material such as aluminum or one of its alloys to avoid unwanted disturbances in the magnetic field established within the reaction vessels. The magnets of the array 16 and the backing material are fastened to the support structure 50 in a variety of ways, including via the use of adhesive or mechanical fasteners. The support structure 50 is itself suspended by being mechanically attached to a wall of an enclosure (not illustrated), either by adhesive, mechanical fasteners, or some combination thereof.

In the illustrated embodiment of the support structure in FIG. 3, the element is segmented into three portions: an initial portion to the right of FIG. 3, a central portion, and a small final portion on the left. The latter provides support for the focusing magnets 28. In an alternative embodiment, the central portion and the final portion are combined, such that the support structure is formed of two portions.

FIG. 3 also illustrates a rear view of the soft magnetic insert 20. Disposed in a central location thereof is a cross-section of a mechanical fastener 52 such as a screw employed in securing the insert 20 to a wall of the enclosure. In alternative embodiments, the soft magnetic insert is supported by a respective support element such as a stanchion or by an extension of the array magnet support element 50. In the latter alternative, the support element 50 would then be one continuous element, if the final portion and the central portion are continuous, or two elements if the focusing magnets 24 is supported independently.

Figure 4A:
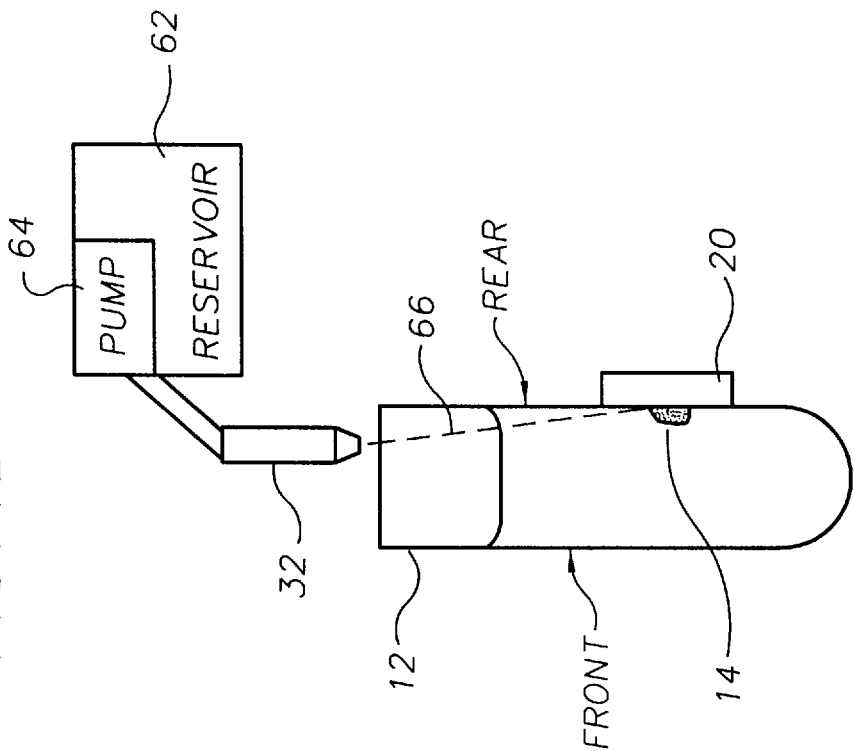
FIG. 4A is a side elevation view of a non-resuspension wash nozzle oriented proximate a reaction vessel for use in the magnet array of FIG. 1A.
Figure 4B:
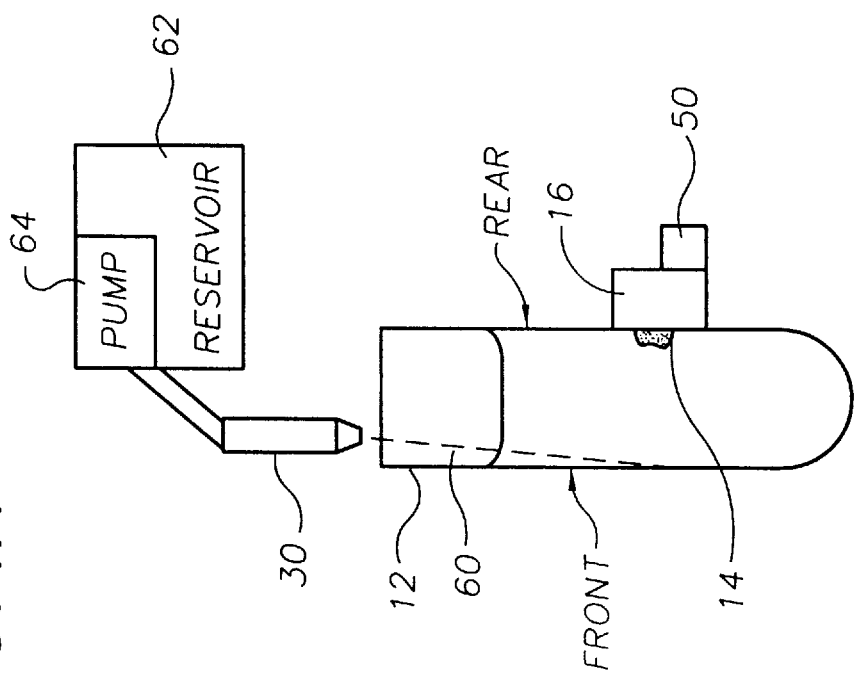
FIG. 4B is a side elevation view of a resuspension wash nozzle oriented proximate a reaction vessel for use in the magnet array of FIG. 1B.

The orientation of wash buffer nozzles as employed along the magnet array 16 of the foregoing is illustrated in FIGS. 4A and 4B. In particular, a nozzle 30 such as that used for reintroduction of wash buffer at position F in FIGS. 1A or 1B is shown in cross-section in FIG. 4A. Solid phase 14 has collected proximate the magnet array 16 (supported by the support element 50) at the rear of the reaction vessel 12. The nozzle 30 is oriented with respect to the reaction vessel 12 to provide a stream 60 of wash buffer from a wash buffer reservoir 62 via a pump 64 to a front, interior surface of the reaction vessel 12. This avoids disturbing the solid phase collected at the rear of the vessel 12.

In FIG. 4B, the orientation of a nozzle 32 such as that used for resuspension wash at position H in FIG. 1B is illustrated in FIG. 4B. A stream 66 of wash buffer from the reservoir 62 via the pump 64 is directed at the solid phase previously collected proximate magnets in the array 16, but now adjacent the soft magnetic insert 20. The solid phase is therefore not retained by magnets, and is easily washed back into suspension by the stream 66 of wash buffer from the nozzle 32.

Having described preferred embodiments of the invention, it will be apparent to those skilled in the art that other embodiments incorporating the concepts may be used.

For instance, though the present invention has been described in the context of a chemiluminescent immunoassay, it can be applied to other assay environments in which the separation of bound and unbound components by magnetic separation is required. Further, the exact number of positions in which magnetizable particles are exposed to magnets 16 depends upon the exact nature of the desired separation, the configuration of the magnets 16, the characteristics of the magnetizable particles and the associated bound component, etc.

Nozzle 32 has been shown in two locations in FIGS. 1A and 1B, specifically position H in FIG. 1A and position I in FIG. 1B. While provided as one nozzle with a like reference identifier in both figures, each embodiment of FIG. 1A and 1B could be provided with a nozzle at position G for non-resuspension wash, and another nozzle at position H for use in an embodiment employing resuspension wash. Thus, the same array configuration could be used for assays both employing and not employing resuspension wash.

In addition to the illustrated embodiment of FIG. 2, other means for translating the conveyor belt are envisioned, such as a friction drive disposed on either side of the conveyor at one or more positions.

In yet another embodiment of the present invention, the reaction vessels 12 are translated along the magnet array 16 by way of a sequence of respective reaction vessel yokes (not illustrated) connected to the respective reaction vessel near the top of the vessel.

The arrangement of elements in FIGS. 4A and 4B is a generalized illustration of the relationship between the elements, and is not intended to represent a preferred layout. For instance, the nozzle 30, 32 in FIGS. 4A and 4B can also be located at the same relative position above a respective reaction vessel 12, but angled in opposite directions to properly direct the respective stream 60, 66. Further, the pump and reservoir can be provided in a variety of ways, as known to one skilled in the art.

These and other examples of the invention illustrated above are intended by way of example and the actual scope of the invention is to be determined from the following claims.

What is claimed is:
1. A wash block, for use in an assay apparatus having a magnet array for clustering magnetic particles on a wall of a reaction vessel, wherein:
  said magnet array comprises plural reaction vessel positions, each position having a magnet adjacent to it, past which said reaction vessel transits in sequence; and
  said magnetic particles have sample components bound to their surfaces, comprising:
  first, second and third consecutive reaction vessel positions;
  a soft magnetic insert; and
  trimmed magnets, wherein:
    said soft magnetic insert is disposed adjacent to said second reaction vessel position and overlaps at least a portion of said first and third reaction vessel positions;
    said trimmed magnets are disposed adjacent to each of said first and third reaction vessel positions; and
    said trimmed magnets are trimmed relative to said magnets of said magnet array, to accommodate said soft magnetic insert which overlaps said first and third reaction vessel positions, such that said magnetic particles are clustered toward the center of said reaction vessel wall proximate said trimmed magnets.

2. The wash block of claim 1, further comprising:
  a tube adjacent to said first vessel position, for inserting into said reaction vessel and aspirating a liquid phase therefrom; and
  a nozzle adjacent to said second vessel position, for dispensing a wash buffer into said reaction vessel.

3. The wash block of claim 2, wherein said nozzle is angled away from said magnetic particles clustered on said reaction vessel wall, to avoid dislodging said magnetic particles, thereby providing a non-resuspension wash of said magnetic particles.

4. The wash block of claim 2, wherein said nozzle is angled toward said magnetic particles clustered on said reaction vessel wall, to dislodge said magnetic particles, thereby providing a resuspension wash of said magnetic particles.

5. The wash block of claim 1, wherein said soft magnetic insert is formed of low carbon steel.

6. An assay apparatus, for separating and washing of magnetic particles in a reaction vessel, wherein said magnetic particles have sample components bound to their surfaces, comprising:
  a magnet array comprising plural upstream reaction vessel positions and plural downstream reaction vessel positions, wherein:
    each reaction vessel position has a magnet adjacent to it, past which said reaction vessel transits in sequence; and
    each of said magnets are comprised of a pair of magnets of oppositely oriented polarity, one above the other, such that said magnetic particles are collected into a band on
  a wall of said reaction vessel proximate the junction of said pair of magnets; and
  a wash block disposed between said plural upstream reaction vessel positions and said plural downstream reaction vessel positions, comprising:
  first, second and third consecutive reaction vessel positions;
  a soft magnetic insert; and
  trimmed magnets, wherein:
    said soft magnetic insert is disposed adjacent to said second reaction vessel position and overlaps at least a portion of said first and third reaction vessel positions;
    said trimmed magnets are disposed adjacent to each of said first and third reaction vessel positions; and
    said trimmed magnets are trimmed relative to said magnets of said magnet array, to accommodate said soft magnetic insert which overlaps said first and third reaction vessel positions, such that said magnetic particles are clustered toward the center of said reaction vessel wall proximate said trimmed magnets.

7. The assay apparatus of claim 6, further comprising a focusing reaction vessel position having a focusing magnet adjacent to it, wherein:

said focusing reaction vessel position is located subsequent to said plural downstream reaction vessel positions; and said focusing magnet has a width less than that of said reaction vessel.

8. The assay apparatus of claim 7, further comprising:

a tube, for inserting into said reaction vessel and aspirating a liquid phase therefrom at said focusing reaction vessel position; and a reagent dispensing nozzle, for dispensing an assay reagent into said reaction vessel at a further reaction vessel position, wherein said nozzle is angled toward said magnetic particles clustered on said reaction vessel wall, to dislodge said magnetic particles, thereby dispersing said magnetic particles into said assay reagent.

9. The assay apparatus of claim 6, further comprising plural non-resuspension washing positions each comprising:

a tube, for inserting into said reaction vessel and aspirating a liquid phase therefrom; and a nozzle, for dispensing a wash buffer into said reaction vessel, wherein:

said tube and nozzle are located adjacent to a respective reaction vessel position; and said nozzle is angled away from said magnetic particles clustered on said reaction vessel wall, to avoid dislodging said magnetic particles, thereby providing a non-resuspension wash of said magnetic particles.

10. The assay apparatus of claim 6, wherein said wash block further comprises:

a tube adjacent to said first vessel position, for inserting into said reaction vessel and aspirating a liquid phase therefrom; and a nozzle adjacent to said second vessel position, for dispensing a wash buffer into said reaction vessel.

11. The assay apparatus of claim 10, wherein said nozzle is angled away from said magnetic particles clustered on said reaction vessel wall, to avoid dislodging said magnetic particles, thereby providing a non-resuspension wash of said magnetic particles.

12. The assay apparatus of claim 10, wherein said nozzle is angled toward said magnetic particles clustered on said reaction vessel wall, to dislodge said magnetic particles, thereby providing a resuspension wash of said magnetic particles.

13. The assay apparatus of claim 6, wherein said soft magnetic insert is formed of low carbon steel.

14. The assay apparatus of claim 6, further comprising a linked conveyor belt comprised of a sequence of reaction vessel receptacles, for translation of said reaction vessel along said magnet array.

15. A method for separating and washing of magnetic particles in a reaction vessel, wherein said magnetic particles have sample components bound to their surfaces, comprising:

passing said reaction vessel through an assay apparatus comprising a magnet array and a wash block, for separating said magnetic particles from a liquid phase in said reaction vessel and washing said magnetic particles free of unbound sample components, wherein:

said magnet array comprises plural upstream reaction vessel positions and plural downstream reaction vessel positions, each reaction vessel position having a magnet adjacent to it, past which said reaction vessel transits in sequence;

each of said magnets are comprised of a pair of magnets of oppositely oriented polarity, one above the other, such that said magnetic particles are collected into a band on a wall of said reaction vessel proximate the junction of said pair of magnets;

said wash block is disposed between said plural upstream reaction vessel positions and said plural downstream reaction vessel positions; and said wash block comprises:

first, second and third consecutive reaction vessel positions;

a soft magnetic insert; and trimmed magnets, wherein:

said soft magnetic insert is disposed adjacent to said second reaction vessel position and overlaps at least a portion of said first and third reaction vessel positions;

said trimmed magnets are disposed adjacent to each of said first and third reaction vessel positions; and said trimmed magnets are trimmed relative to said magnets of said magnet array, to accommodate said soft magnetic insert which overlaps said first and third reaction vessel positions, such that said magnetic particles are clustered toward the center of said reaction vessel wall proximate said trimmed magnets.

16. The method of claim 15, wherein:

said assay apparatus further comprises a focusing reaction vessel position having a focusing magnet adjacent to it, through which said reaction vessel is passed;

said focusing reaction vessel position is located subsequent to said plural downstream reaction vessel positions; and said focusing magnet has a width less than that of said reaction vessel, for further localizing said magnetic particles.

17. The method of claim 16, wherein said assay apparatus further comprises:

a tube, for inserting into said reaction vessel and aspirating a liquid phase therefrom at said focusing reaction vessel position, and a reagent dispensing nozzle, for dispensing an assay reagent into said reaction vessel at a further reaction vessel position, wherein:

said nozzle is angled toward said magnetic particles clustered on said reaction vessel wall; and said magnetic particles are thereby dislodged and dispersed into said assay reagent.

18. The method of claim 15, wherein said assay apparatus further comprises plural non-resuspension washing positions comprising:

a tube, for inserting into said reaction vessel and aspirating a liquid phase therefrom; and a nozzle, for dispensing a wash buffer into said reaction vessel, wherein:

said tube and nozzle are located adjacent to plural reaction vessel positions; and said nozzle is angled away from said magnetic particles clustered on said reaction vessel wall, to avoid dislodging said magnetic particles, thereby providing a non-resuspension wash of said magnetic particles.

19. The method of claim 15, wherein said wash block further comprises:
   a tube adjacent to said first vessel position, for inserting into said reaction vessel and aspirating a liquid phase therefrom; and
   a nozzle adjacent to said second vessel position, for dispensing a wash buffer into said reaction vessel, thereby washing said magnetic particles.

20. The method of claim 19, wherein said nozzle is angled away from said magnetic particles clustered on said reaction vessel wall, to avoid dislodging said magnetic particles, thereby providing a non-resuspension wash of said magnetic particles.

21. The method of claim 19, wherein said nozzle is angled toward said magnetic particles clustered on said reaction vessel wall, to dislodge said magnetic particles, thereby providing a resuspension wash of said magnetic particles.

22. The method of claim 15, wherein said soft magnetic insert of said wash block is formed of low carbon steel.

23. The method of claim 15, wherein said assay apparatus further comprises a linked conveyor belt comprised of a sequence of reaction vessel receptacles, thereby translating of said reaction vessel along said magnet array.

* * * * *

UNITED STATES PATENT AND TRADEMARK OFFICE
CERTIFICATE OF CORRECTION

PATENT NO. : 5,888,835
DATED : March 30, 1999
INVENTOR(S) : Steven E. Bushnell et al.

Page 1 of 1

It is certified that error appears in the above-identified patent and that said Letters Patent is hereby corrected as shown below:

<u>Column 3,</u>
Line 63, "4B" should read -- 4A --.

Signed and Sealed this

Fourteenth Day of May, 2002

*Attest:*

*Attesting Officer*

JAMES E. ROGAN
*Director of the United States Patent and Trademark Office*